United States Patent [19]

Draper

[11] 4,275,940

[45] Jun. 30, 1981

[54] UTILITY CABINET FOR DENTISTS

[76] Inventor: Leonard C. Draper, 3819 Kings Dr., Douglasville, Ga. 30135

[21] Appl. No.: 56,898

[22] Filed: Jul. 12, 1979

[51] Int. Cl.³ .......................... A61C 19/02; A47B 81/00; A61B 19/02

[52] U.S. Cl. .......................................... 312/209; 108/83; 108/137; 248/296; 248/297.5; 292/74; 292/DIG. 46; 312/301; 312/348; 433/79

[58] Field of Search ............... 312/209, 301, 308, 348, 312/250, 249; 433/77, 79; 108/83, 102, 137, 143; 292/DIG. 46, 74; 248/296, 295 C, 289 R; 5/503

[56] References Cited

U.S. PATENT DOCUMENTS

| | | | |
|---|---|---|---|
| 2,449,433 | 9/1948 | Wheelock | 312/301 |
| 2,682,932 | 7/1954 | Howard | 312/204 |
| 2,730,423 | 1/1956 | Mock | 312/348 |
| 3,321,068 | 5/1967 | Beach | 248/205 R |
| 3,423,057 | 1/1969 | Iverson | 248/296 |
| 3,708,709 | 1/1973 | Morrison et al. | 312/209 |
| 4,130,070 | 12/1978 | Herrin | 108/143 |

OTHER PUBLICATIONS

"Valtronic", Catalog-6/1970, Model NZ MSFL-Val-LR, P. 6.

*Primary Examiner*—Alexander Grosz
*Attorney, Agent, or Firm*—James B. Middleton

[57] ABSTRACT

An improved utility cabinet for dentists is disclosed. The top of the cabinet is movable to a closed position and a functional position, and an adjustable, spring-urged bolt is engageable with different escutcheon plates to latch the top in each position. A waste receptacle is attachable to the side of the cabinet by a hook and teazle material for simplicity in releasably attaching the receptacle to the cabinet. An optional arm rest is arranged so bracket arms spring inwardly against collars to retard pivotal motion of the arm rest.

4 Claims, 6 Drawing Figures

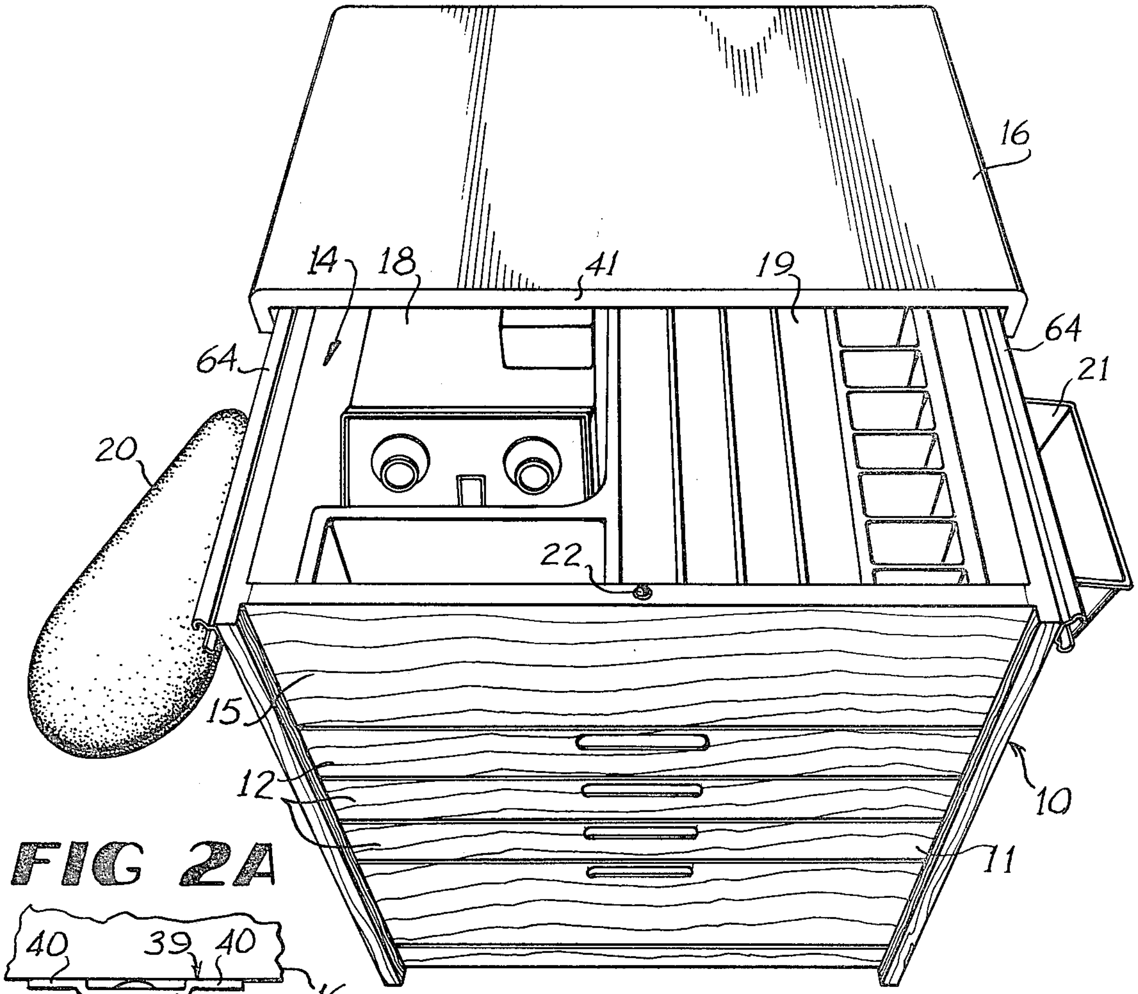
FIG 1
FIG 2A
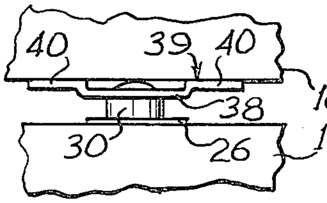
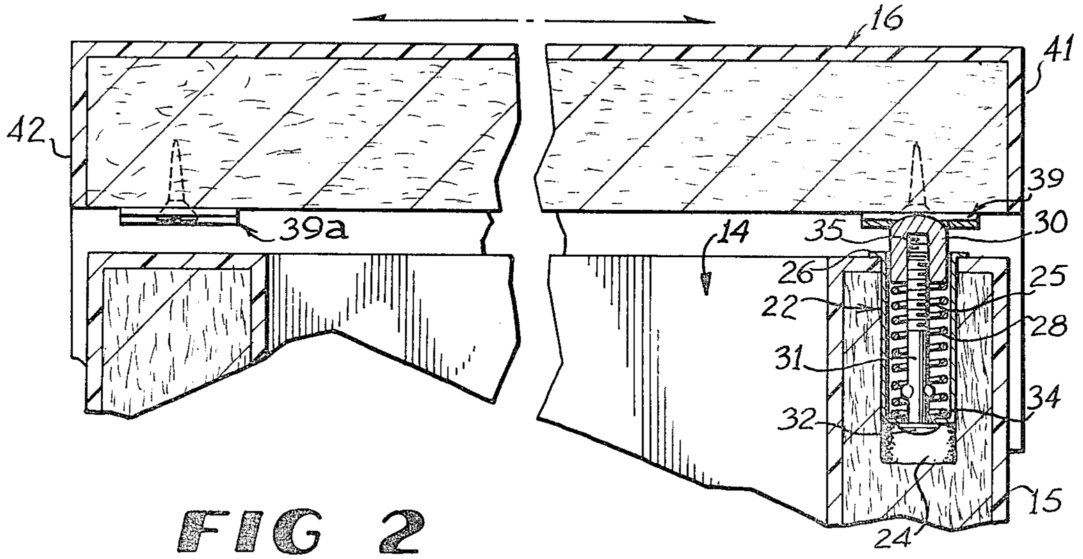
FIG 2

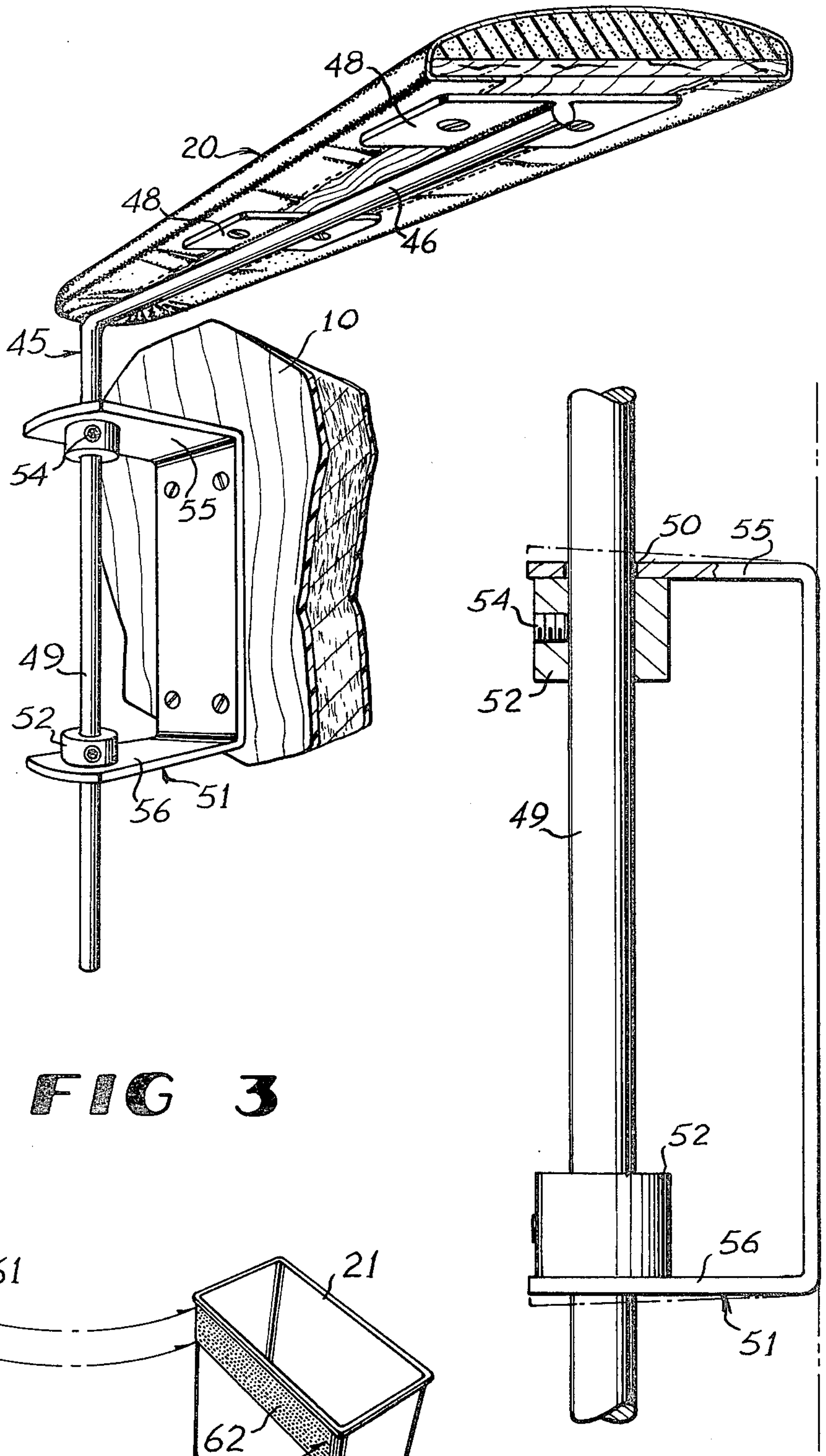
FIG 3
FIG 4
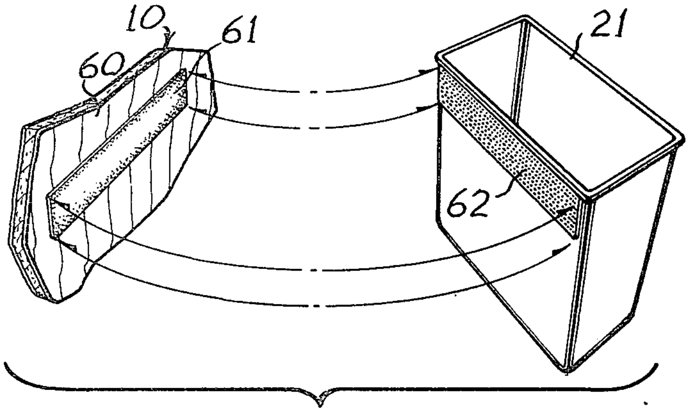
FIG 5

UTILITY CABINET FOR DENTISTS

FIELD OF THE INVENTION

This invention relates to utilitarian cabinets, and is more particularly concerned with a utility cabinet for use by dentists.

BACKGROUND OF THE INVENTION

For many years the manner in which dentists have worked, and their cabinet requirements, remained very much the same. More recently, however, there have been efforts to arrange a dentist's work area to be more efficient; also, in arranging this efficiency there has been greater and greater use of assistants. Due to this use of assistants, the work area for the dentist must of course provide for efficiency for both the dentist and the dentist's assistant.

There have arisen two primary styles of dentistry utilizing assistants, these being known generally as the Alabama Method and the North Carolina Method. In both these methods, the technique utilizes a utility cabinet at which the assistant sits, the cabinet being immediately adjacent to the dentist. The cabinet becomes an integral part of the total work arrangement so that it is extremely important to have a well built and well designed cabinet.

In cabinets for both the Alabama Method and the North Carolina Method, one of the necessary features is a movable top for the cabinet, the top being movable to a closed position in which the cabinet is generally out of service, and to a shifted, or functional, position. Since, in the closed position, the cabinet is frequently being moved from one location to another it is rather important that the top be reasonably well secured in such position; further, when the cabinet is in its functional position, the assistant utilizes the top of the cabinet as a work counter so that it is extremely important that the top be reasonably well secured in this position.

Since one of the objects to be achieved is maximum efficiency, it is also important that the waste receptacle be conveniently placed with respect to the cabinet, and it is now conventional in the prior art to have a waste receptacle fixed to the side of the cabinet.

In the past, the latches for the tops of the cabinets have been sufficiently insecure that, when a technician was attempting to stir or mix in the course of the normal duties, the top of the cabinet tended to latch and unlatch. This allowed the top to shake, and become a great disturbance to the technician rather than an assistance to the technician. Also, the waste receptacle has been fixed on the side of the cabinet in a convenient location; but, the brackets by which the receptacle has been fixed to the side of the cabinet have been rather complex, and frequently require two hands to fix the receptacle to the cabinet. This is highly undesirable since the technician may wish to empty the waste receptacle without completely letting go of the work being done.

In using the Alabama Method, some dentists utilize an arm rest to brace themselves to remain steady while working on a patient. While the arm rest should always be movable so any given dentist can achieve maximum comfort for his particular working technique, the arm rest should not be so easily movable as to be moved inadvertently, or to wave back and forth during transportation of the cabinet.

SUMMARY OF THE INVENTION

The present invention overcomes the above mentioned and other difficulties with the prior art utility cabinets for dentists by providing a cabinet which can be constructed either as an Alabama Model or as a North Carolina Model. The movable top is provided with latching means to latch the movable top in either the closed position or the functional position, the latch being adjustable to provide the desired latching force. Nevertheless, the latch is arranged with a sloped surface coacting with an escutcheon plate, the escutcheon plate being arranged to contact the latching member on a part of the sloped surface to provide a sufficient locking arrangement while allowing the latching mechanism to unlatch when a reasonable amount of intentional force is exerted thereon. While the location of the waste receptacle is substantially conventional in the present invention, a mounting means for the waste receptacle is provided whereby the receptacle can be fixed with respect to the cabinet in a plurality of different positions, and in slightly different locations. More specifically, the waste receptacle is attachable to the side of the cabinet by hook and teazle strips, the teazle means being fixed to the side of the cabinet, preferably in an elongated strip. A similar strip of hook means is fixed to a side of the waste receptacle, preferably near the upper edge thereof. Since the waste receptacle is generally rather light in weight, virtually any contact between the hook members and the teazle will provide a sufficient holding force to sustain the waste receptacle in place. The arm rest is also maintained in its desired position by the very simple but clever expedient of providing a spring urged force on the collars that determine the vertical placement of the arm rest. The present invention therefore combines the vertically adjustable feature with means to prevent inadvertent lateral or pivotal displacement of the arm rest.

BRIEF DESCRIPTION OF THE DRAWINGS

These and other features and advantages of the present invention will become apparent from consideration of the following specification when taken in conjunction with the accompanying drawings in which:

FIG. 1 is a perspective view of a cabinet constructed in accordance with the present invention, the cabinet being shown with the top moved rearwardly to expose the interior of the cabinet;

FIG. 2 is a partial, longitudinal cross-sectional view of the cabinet of FIG. 1 on an enlarged scale to show the latch;

FIG. 2A is a partial, front elevational view illustrating the relation between the latch member and the escutcheon plate;

FIG. 3 is a perspective view showing the arm rest made in accordance with the present invention, the arm rest being partially in cross-section;

FIG. 4 is a side elevational view of the mounting means for the arm rest, partially shown in cross-section; and, FIG. 5 is a perspective view showing the attaching means for the waste receptacle.

DESCRIPTION OF THE PREFERRED EMBODIMENT

Referring now more particularly to the drawings, and to that embodiment of the invention here chosen by way of illustration, in FIG. 1 it will be seen that there is a cabinet generally designated at 10 having four walls including a front 11 which is provided with a plurality of drawers 12. The upper compartment 14 of the cabinet 10 includes a rigid front panel 15, access to the compartment 14 being through the open top. In FIG. 1 it will be seen that the top 16 is moved rearwardly to expose the contents of the compartment 14. As is conventional, the top compartment 14 includes an amalgamator 18 and a tray 19 which are used frequently during various dental procedures.

As viewed in FIG. 1, the left side of the drawing shows the arm rest 20, and the right side illustrates the waste receptacle 21. Centrally of the fixed wall 15 of the front 11, the latching member 22 is shown.

Attention is now directed to FIGS. 2 and 2A of the drawing which show the latching member 22 in more detail. It will be seen that the panel 15 has a hole 24 provided therein, the hole 24 being of such size to receive the latching member 22.

The latching member 22 includes a barrel 25 having a flange 26 at the upper edge thereof, the arrangement being such that the barrel 25 is received in the hole 24, and the flange 26 rests on the upper edge of the wall 15 to limit the downward movement of the barrel 25.

Within the barrel 25 there is a spring 28, one end of which bears against the bottom 29 of the barrel 25, and the other end of which bears against the bolt 30. Extending through the spring 28, generally axially thereof, there is a screw 31 having a head 32 which is of a greater diameter than the hole 34 in the bottom 29 of the barrel 25. This arrangement limits the upward movement of the screw 31.

The upper end of the screw 31 is threaded; and, an internal bore 35 of the bolt 30 is threaded, the threads in the bore 35 being complementary with the threads on the bolt 31. Because of this arrangement, it will be understood that rotation of the bolt 30 will cause the bolt 30 to move up or down with respect to the screw 31. The advantages of this arrangement will be discussed in more detail hereinafter.

Attention is next directed to the escutcheon plate 39 which cooperates with the bolt 30. It will be seen that the central portion 38 of the escutcheon plate is spaced downwardly from the lower surface of the top 16. The flanges 40 are here shown as off-set from the section 38 to provide the appropriate spacing; however, it will be understood by those skilled in the art that appropriate spacers or the like may be placed under a conventional flat escutcheon plate in order to achieve the desired spacing of the central portion 38.

It will be realized that the operating end of the bolt 30 has a somewhat spherical configuration. As a result, the closer to the top of the bolt 30 the escutcheon plate 39 strikes, the less will be the slope of the bolt at that particular point, since the slope of a spherical surface approaches zero at the diameter. One will also realize that the less the slope, the greater the mechanical advantage so that the escutcheon plate 38 would move the bolt 30 downwardly very easily against the tension of the spring 28.

While it is common in the art to provide a mortise for receiving a bolt such as the bolt 30, it should be understood that, in the present situation, there is no means for holding the bolt 30 in a retracted position other than the force of the top 16. Therefore, if a mortise is provided to receive the bolt 30, the lower surface of the top 16 would be the means for holding the bolt 30 in its retracted position, and this would cause a scoring on the underside of the top 16. The scoring would be undesirable in that it would mar the surface; however, it would also be undesirable in that there would be an additional drag in moving the top 16 from one position to another, and the additional wear on the bolt 30 would shorten the life of the bolt 30. It will also be realized that the interior of the cabinet 10 should remain free of debris, and the bolt's dragging across the underside of the top 16 would probably release a number of fibers from the board from which the top is made, thereby causing a constant rain of debris into the interior of the cabinet.

With the constant force of the spring 28 against the bolt 30, if the bolt 30 is rotated to unscrew the bolt from the screw 31, the uppermost end of the bolt 30 will be higher. Conversely, if the bolt 30 is rotated to screw the bolt 30 on to the screw 31, the uppermost end of the bolt 30 will be lower. As the position of the bolt 30 is varied, the slope of the surface engaged by the escutcheon plate will be varied, and the distance the bolt must move for complete unlatching will be varied. The result is that the ease of latching and unlatching, and the security of the latch, can be varied by rotation of the bolt 30.

The two positions of the top 16 have been previously mentioned, and it will be seen in FIG. 2 that there is a first escutcheon plate 39 located adjacent to the front edge 41 of the top 16. This escutcheon plate allows the top 16 to be latched in the closed position. A second position in which the cabinet would be utilized is the position in which the top 16 is moved forward to the functional position so that an assistant can sit at the front of the cabinet 10 and use the top 16 as a work space, the forward projection of the top 16 providing knee space for the assistant. In this position of course the assistant has the drawers 12 accessible in the event additional supplies or instruments are needed. In order to latch the top 16 in this forward position, there is a second escutcheon plate 39*a* here shown as located adjacent to the rear edge 42 of the top 16. It will be understood that the precise placement of the escutcheon plate 39*a* could be varied depending on the precise position of the top 16 desired.

Looking now at FIGS. 3 and 4 of the drawing, it will be seen that the arm rest 20 is carried by an L-shaped rod 45 having a horizontal portion 46 fixed to the underside of the arm rest 20 by appropriate brackets 48. The vertical portion 49 of the L-shaped rod 45 is rotatably received through holes, such as the hole 50, in a U-shaped bracket member 51. This arrangement provides the basic rotatable mounting of the arm rest 20, it being understood that the arm rest 20 will rotate about the vertical portion 49 of the L-shaped rod 45; and, the rod 45 can be adjusted vertically, the vertical portion 49 of the rod being moved with respect to the bracket 41 to achieve the desired height of the arm rest 20.

To maintain the desired position of the arm rest 20 with respect to the bracket 51, there is a pair of collars 52 which surround the portion 49 of the rod 45 and are fixed in place by set screws 54.

With the above described arrangement, it will be understood that the arm rest 20 will be freely rotatable. To overcome this, the present invention provides the bracket 51 which is to be made of stainless steel or a comparable material having sufficient strength and elasticity that the upper and lower arms 55 and 56 can be flexed outwardly during the placement of the collars 52. More precisely, the lower collar 52 may be located as desired to achieve the proper height of the arm rest 20, then the upper collar 52 can be pushed against the upper arm 55 of the bracket 51, then forcefully urged somewhat further upwardly along the vertical portion 49 of the rod 45. While holding the collar 52 in this position, with the arms 55 and 56 of the bracket 51 forced outwardly, the screw 54 for the upper collar 52 will be tightened to hold the collar 52 in place. The elastic force of the bracket 51 will then press against the collars 52 to increase the coefficient of friction sufficiently that the arm rest 20 is held from inadvertent rotation. Also, it will be seen that the arm rest 20 is easily movable as before, there being no additional manipulations required by the present invention.

Looking finally at FIG. 5 of the drawing, it will be seen that the side wall 60 of the cabinet 10 is shown fragmentarily, the side wall 60 including an elongated strip 61 of teazle material. The waste container 21 is here shown as a generally rectangular receptacle having an elongated strip 62 fixed to the upper edge of one of the sides of the container. The strip 62 comprises a plurality of hooks to cooperate with the teazle on the strip 61. Those skilled in the art will understand the hook and teazle arrangement, such material being sold under the trademark "Velcro." It will also be understood that the hook and teazle material has sufficient strength that a rather small portion of the total material shown would be sufficient to support the waste receptacle 21, even with a considerable amount of the usual waste therein. Because of this, the receptacle 21 does not have to be carefully aligned, with the strips 61 and 62 precisely overlapping each other; rather, the receptacle 21 can be hurriedly moved against the strip 61 in almost any orientation desired, and there will still be sufficient holding force to retain the receptacle 21. As a result, it will be seen that the receptacle 21 may be sloped for more convenient access, or may be moved closer to the front or rear of the cabinet 10. Since the hook and teazle material will hold by merely touching the two strips together, the waste receptacle 21 can be attached to the cabinet even by a very inattentive assistant, so the assistant's attention can remain on the dental work rather than on the manipulation of the waste receptacle.

It will therefore be seen that the present invention provides a greatly improved utility cabinet for dentists and the like. While the cabinet here presented by way of illustration is of the Alabama type, those skilled in the art will readily understand that the runners 64 for the top 16 can be mounted on the front and rear of the cabinet so that the top 16 would move to the side rather than to the front or rear, and the cabinet would be of the North Carolina type. The escutcheon plates 39 and 39*a* can be installed as desired to place the top 16 in virtually any position desired by the dentist and his assistant.

It will of course be understood by those skilled in the art that the particular embodiment of the invention here presented is by way of illustration only, and is meant to be in no way restrictive, therefore, numerous changes and modifications may be made, and the full use of equivalents resorted to, without departing from the spirit or scope of the invention as defined in the appended claims.

I claim:

1. A utility cabinet, for dentists and the like, comprising four walls and a top, a pair of runners carried by two of said walls and carrying said top such that said top is movable with respect to said cabinet, said top having a closed position with respect to said cabinet and a functional position with respect to said cabinet, and latch means for latching said top in at least one of said positions, characterized in that said latch means includes a bolt mounted in one of said walls, said bolt having a surface with varying slope, spring means for urging said bolt towards the lower surface of said top, stop means for preventing said bolt from touching said lower surface of said top, and an escutcheon plate carried by said lower surface of said top, said escutcheon plate being spaced from said lower surface and located for engagement by said bolt.

2. A utility cabinet as claimed in claim 1, said bolt being adjustably mounted for selective movement towards and away from said lower surface for varying the portion of said surface of said bolt to be engaged by said escutcheon plate, said escutcheon plate being located adjacent to a first edge of said top for engagement with said bolt when said top is in said closed position, and further characterized by a second escutcheon plate adjacent to a second edge of said top for engagement with said bolt when said top is in said functional position.

3. A utility cabinet as claimed in claim 2, and further characterized by a waste receptacle selectively receivable on said cabinet, said cabinet including an elongated strip of teazle material fixed thereto, said waste receptacle including an elongated strip of hook means fixed thereto cooperable with said strip of teazle material, said functional position of said top being a position in which said top is moved forwardly with respect to said cabinet, said strip of teazle material being fixed to a side of said cabinet so that said waste receptacle is selectively receivable on said side of said cabinet.

4. A utility cabinet for dentists and the like, comprising four walls and a top, a pair of runners carried by two of said walls carrying said top such that said top is movable with respect to said cabinet, said top having a closed position with respect to said cabinet and a functional position with respect to said cabinet, and latch means for latching said top in at least one of said positions, characterized in that said latch means includes a bolt mounted in one of said walls, said bolt having a surface with varying slope, spring means for urging said bolt towards the lower surface of said top, and an escutcheon plate carried by said lower surface of said top, said escutcheon plate being spaced from said lower surface and located for engagement by said bolt, and wherein said functional position of said top is a position in which said top is moved forwardly with respect to said cabinet, and said cabinet includes an arm rest carried by a side of said cabinet, characterized by retarding means for preventing inadvertent motion of said arm rest, said arm rest including a vertical member for adjustably mounting said arm rest, a bracket having upper and lower arms for rotatably receiving said vertical member, collars selectively fixable on said vertical member between said arms, said bracket being formed of elastic material, said arms being forced outwardly before fixing said collars to said vertical member so that said arms act against said collars to provide said retarding means.

* * * * *